United States Patent [19]

Buttery et al.

[11] Patent Number: 4,522,838
[45] Date of Patent: Jun. 11, 1985

[54] 2-ACETYL-1-PYRROLINE AND ITS USE FOR FLAVORING FOODS

[75] Inventors: Ronald G. Buttery; Louisa C. Ling, both of El Cerrito, Calif.; Bienvenido O. Juliano, Los Banos Laguna, Philippines

[73] Assignees: The United States of America as represented by the Secretary of Agriculture, Washington, D.C.; International Rice Research Institute, Republic of the Philippines, Los Banos, Philippines

[21] Appl. No.: 500,049

[22] Filed: Jun. 1, 1983

[51] Int. Cl.$^3$ .................... C07D 207/00; A23L 1/226
[52] U.S. Cl. .................................................. 426/537
[58] Field of Search ........................ 426/537; 548/540

[56] References Cited

U.S. PATENT DOCUMENTS 3,336,138  8/1967  Nakel ................................. 426/537
3,620,771 11/1971  Hunter et al. .................. 426/537 X
3,725,425  4/1973  Hunter et al. .................. 426/537 X

OTHER PUBLICATIONS

Yajima, Yanai, Nakamura, Sakakibara, and Hayashi, "Volatile Flavor Components of Cooked Kaorimai (Scented Rice, O. sativa japonica)," *Agricultural and Biological Chemistry*, vol. 43(12), pp. 2424–2429 (1979).
Yajima, Yanai, Nakamura, Sakakibara, and Habu, "Volatile Flavor Components of Cooked Rice," *Agricultural and Biological Chemistry*, vol. 42(6), pp. 1229–1233 (1978).
Tsugita, Kurata and Kato, "Volatile Components After Cooking Rice Milled to Different Degrees," *Agricultural and Biological Chemistry*, vol. 44(4), pp. 835–840 (1980).
Tsugita, Kurata and Fujimaki, "Volatile Components in the Steam Distillate of Rice Bran: Identification of Neutral and Basic Compounds, *Agricultural and Biological Chemistry*, vol. 42(3) pp. 643–651 (1978).
Buchi and Wuest, "Synthesis and 2-Acetyl-1,4,5,6-tetrahydropyridine, a Constituent of Bread Aroma, *Journal of Organic Chemistry*, vol. 36(4) (1971).
Guadagni and Buttery, "Odor Threshold of 2,3,6–trichloroanisole in Water," *Journal of Food Science*, vol. 43, 1346–1347 (1978).
Buttery et al., *2–Acetyl-1–Pyrroline: An Important Aroma Component of Cooked Rice*, Chemistry and Industry, Dec. 4, 1982, pp. 958–959.

*Primary Examiner*—Joseph Golian
*Attorney, Agent, or Firm*—M. Howard Silverstein; David G. McConnell; Margaret A. Connor

[57] ABSTRACT

The compound, 2-acetyl-1-pyrroline and its use in flavoring foods, particularly in imparting a "scented" rice flavor to foods, are disclosed.

8 Claims, No Drawings

2-ACETYL-1-PYRROLINE AND ITS USE FOR FLAVORING FOODS

BACKGROUND OF THE INVENTION

This invention relates to the novel compound 2-acetyl-1-pyrroline and its use for flavoring foods, particularly in imparting a "scented" rice flavor to foods.

In the food industry, it is well recognized that flavor and aroma play a critical role in the value of food products for consumption. Aroma also plays an important role in insect perception of a food and knowledge of the identity of important aroma components of a food is useful in preventing insect infestation.

Aroma and flavor are particularly important in the consumption of rice and products made therefrom. A considerable number of varieties of rice are grown throughout the world with a variation in the degree of aroma and flavor. Consumers from different parts of the world or heritage vary as to rice variety preference. For example, Texas Long Grain rice or Calrose rice varieties grown in the U.S. are considered to have a "bland" flavor and aroma; these varieties are popular with many U.S. consumers. In contrast, rice varieties such as Basmati, Milagrosa, and Malagkit Sungsong varieties which exhibit a more intense "aromatic" flavor and aroma (denoted as a "scented" rice flavor and aroma) are preferred by consumers in or from South East and East Asia, e.g., India, the Philippines, Pakistan, Thailand, Indonesia; the Orient, and the Middle East. In addition to being more aromatic, these varieties are also more costly.

The volatile flavor and aroma components of rice have been intensely investigated by a number of researchers over the years, and although over 100 compounds have been identified as volatile components of cooked rice (see Yajima et al., *Agricultural and Biological Chemistry*, Volume 43 (12), pp 2424–2429 (1979) and Volume 42(6), pp 1229–1233 (1978), and Tsugita et al., *Agricultural and Biological Chemistry*, Volume 44(4), pp 835–840 (1980) and Volume 42(3) pp 643–651 (1978)), no single compound has been identified as exhibiting the aromatic flavor and aroma of the expensive "scented" rice varieties.

SUMMARY OF THE INVENTION

We have now for the first time identified and isolated in pure or substantially pure form the compound 2-acetyl-1-pyrroline which exhibits an intense flavor and aroma typical of the costly "scented" rice varieties. This compound has also been successfully synthesized.

Our invention provides a means for imparting a "scented" rice flavor and aroma to food compositions, particularly "bland" rice varieties or products made therefrom. This novel compound can be used as a flavoring agent for incorporation in food products or for incorporation in flavoring or seasoning compositions. Salts of this compound can be readily formed by contacting it with an acid and the salts formed thereby can also be used as flavoring agents.

Discovery of the identity of an important aroma component of rice is also useful in the understanding of insect infestation of rice as insect pests are known to locate stored rice by keying in on associated volatile odor compounds.

In accordance with our discovery, it is an object of the invention to identify for the first time a compound which exhibits the flavor and aroma that "scented" varieties of rice have after cooking.

Another object of the invention is to provide this compound in pure or substantially pure form.

Further objects of the invention include the use of 2-acetyl-1-pyrroline and salts thereof to impart "scented" rice flavor and aroma to foodstuffs and the use of the compound and its salts as a flavoring ingredient in foodstuffs or in flavor modifying compositions.

Another object of the invention is the provision of the identity of an important aroma component of rice to aid in the understanding and control of insect infestation.

Other objects and advantages of the invention will be evident from the following description wherein parts and percentages are by weight.

DETAILED DESCRIPTION OF THE INVENTION

The compound 2-acetyl-1-pyrroline (hereinafter referred to as APR) for use in this invention has the structural formula:

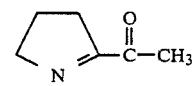

This compound exhibits an intense aroma and flavor typical of expensive aromatic, "scented" rice varieties (after cooking) such as Basmati, Malagkit Sungsong, Milagrosa and the like. APR can be used in minor amounts to flavor foods and foodstuffs, and as used herein, it will be understood that foods and foodstuffs include both solids and liquids. For example, APR can be added to "bland" rice varieties or dishes made from these varieties to provide the desirable flavor and aroma of the aromatic "scented" varieties. Exemplary rice varieties are Calrose, Texas Long Grain, California Short Grain, Pearl, and the like. Exemplary rice-containing dishes include many kinds of pilaf (e.g. Istambouli pilaf, Zereshak pilaf), dolmas, Ferine pudding, riz a' la Indienne, riz a' la Grecque, and the like. APR can also be used to flavor meat and vegetable products or dishes or can be blended with other flavor enhancing sauces or compositions. For example meatloaf, gravies, soups, stews, and ketchup can be flavored with APR. It is also within the compass of the invention to use APR in combination with other flavoring agents. For example, APR can be mixed with known flavoring ingredients such as monosodium glutamate, onion powder, garlic powder, black pepper, paprika, or dried herbs such as parsley, oregano, celery, sage, and the like to form a flavor enhancing composition.

While APR may be added directly to the food or flavoring agent to which the flavor is to be imparted, only very small quantities, on the order of parts per million (ppm), are needed and accordingly, it may first be combined with liquid and solid vehicles or carriers before addition to a food or flavoring ingredient. Examples of such vehicles or carriers are water, ethanol, glycerol, edible fats and oils, starch, sorbitol, salt, sugar, gelatin, flour, powdered skim milk, corn syrup solids, or other physiologically acceptable substances compatible with the material to be flavored.

In the methods of the invention, pure or substantially pure APR is added in a "flavoring amount," that is, in an amount sufficient to impart the desired flavor character and/or other organoleptic properties to the material to be flavored. When it is desirable to enhance the flavor and aroma of "bland" rice varieties to duplicate the flavor and aroma of the more aromatic "scented" rice varieties, then the flavoring amount is that sufficient to impart a "scented" rice flavor and aroma to the rice. APR is ordinarily employed in very minor proportions, for example in a concentration of about 0.001 to 10 ppm. In the flavoring of some foodstuffs, a concentration of 0.005 to 0.5 ppm may be preferred. It is obvious, however, that the concentration to be used depends on the desired flavor level appropriate to the material in question.

APR was synthesized following the procedure used by Buchi and Wuest, *Journal of Organic Chemistry, Volume 36*, pp 609–610 (1971) for the synthesis of a related 6-membered ring compound. Synthesis of APR involved catalytic reduction of 2-acetylpyrrole with rhodium-on-alumina catalyst followed by the oxidation of the intermediate 2-(1-hydroxyethyl)-pyrrolidine with silver carbonate. APR was isolated in pure or substantially pure form by gas liquid chromatography as a clear, colorless liquid which is stable in solution (e.g., water, ethanol) but which in the pure state, turns red on standing.

Stable solid salts of APR are readily prepared by contacting APR (which is an organic base) with an acid using standard procedures. Physiologically acceptable acids suitable for preparing salts of APR for food use include hydrochloric, sulfuric, phosphoric, acetic, citric, fumaric, tartaric, and the like.

When the salt is to be used, APR is readily released therefrom by contact with a basic substance such as sodium bicarbonate, sodium carbonate, calcium carbonate, potassium carbonate, calcium hydroxide, sodium hydroxide, potassium carbonate, or the like. Alternately, the salts of APR can be used as such to flavor foods. They are effective in such flavoring applications because APR is a weak base, hence it is readily released from its salts upon contact with materials having basic or buffering properties such as are normally present in many foods. In utilizing the salts of APR directly as flavoring agents they are incorporated into the food to be flavored in the same manner as described hereinabove in connection with APR in the free base form. In sum, the salts, as such or in a carrier, are incorporated in the food in the amount which yields the desired flavor. Moreover, flavoring compositions can be formed with the salts just as hereinabove described with APR.

APR was found by capillary gas chromatography-mass spectrometry to be present in the volatiles of several varieties of cooked rice. It is to be emphasized that although over 100 compounds had been previously identified as volatile components of cooked rice, prior to our invention APR had not been previously reported in rice or other natural products or in its synthetic form.

A particular advantage of this invention is that it enables the provision of APR in pure form. In this state APR has high and uniform flavoring power and is free from extraneous substances, so that it can advantageously be used, even in very minor proportions for the effective flavoring of food products. In the state APR exists in the steam distillates of cooked rice, it is too dilute for flavoring applications. Also such distillates vary widely in their flavor characteristics so that they cannot be depended upon to yield uniformly flavored food products.

To isolate and identify APR in rice, one of the followed procedures was used. The volatile oil of freshly cooked rice was obtained by vacuum steam distillation continuous extraction with hexane as solvent. Next, the solvent was removed under reduced pressure to yield a volatile oil which was of the order of 1 ppm of the original cooked rice. The oil (handled as solution in hexane) was separated into more than 100 components by gas chromatography (GLC) using a glass capillary column coated with Carbowax 20M. The effluent from the capillary was introduced into a mass spectrometer using a silicone rubber membrane type molecular separator. The compound identified as APR had a mass spectrum and capillary gas liquid chromatography retention time identical to that of synthetic APR prepared as described above.

In an alternate procedure, a 2-hour atmospheric distillation continuous extraction procedure was carried out on uncooked rice. Cooking occurred during the isolation process. The amount of volatile oil obtained by this method was about 5 ppm. The volatile oil was analyzed by capillary GLC-MS and the amount of APR calculated from GLC peak areas.

APR was identified in 10 rice varieties investigated. The highest concentration was found in Malagkit Sungsong (milled rice, 0.09 ppm; brown rice, 0.2 ppm) and the lowest concentration was found in Calrose (milled rice, less than 0.006 ppm). APR occurs at a higher concentration in brown rice than in milled rice of the same variety.

APR showed considerable instability to general gas chromatography conditions and could not be chromatographed using silcone or Carbowax 20M packed columns. This may explain why it was not detected in the earlier studies of rice volatiles. APR seemed reasonably stable using a glass capillary column coated with Carbowax 20M.

The following examples are given to further illustrate the invention and are not intended to limit the scope of the invention which is defined by the claim.

EXAMPLE I

A. Synthesis of APR

2-Acetylpyrrole (1.7 g) in methanol solution (50 ml) was hydrogenated using 5% rhodium on alumina catalyst (2.0 g) at room temperature under 10 psi hydrogen pressure for 15 hours with stirring. Filtration and removal of the solvent by distillation gave the crude intermediate 2-(1-hydroxyethyl)-pyrrolidine (1.8 g). This intermediate showed a mass spectrum with a molecular ion at 115 and other important ions at 70 ($M^+$-45), 69, 68, 54, 97($M^+$-18), 82($M^+$-33) and an infrared spectrum consistent with the structure of this compound. The 2-(1-hydroxyethyl)-pyrrolidine (1.8 g) was added to a stirred suspension of silver carbonate on celite (16 g) in benzene (100 ml) under a nitrogen atmosphere. The mixture was refluxed under nitrogen for 15 hours. Filtration removal of the silver carbonate and concentration by distillation to 5 ml gave a benzene solution of APR which was isolated by gas liquid chromatography (GLC). This indicated an overall yield (from 2-acetylpyrrole) of 10%. The GLC column used was a 2 m long by 0.64 cm o.d. aluminum column packed with 15% Amine 220 on 60–80 mesh Chromosorb P. The GLC purified APR was greater than 95% pure; it was collected in 3 mm o.d. Pyrex tubes, sealed under vacuum and stored at −20° C.

The mass spectrum of APR (above m/e 40, intensities in parentheses with base peak taken as 100) showed a molecular ion at 111(5), other major ions at 43(100), 41(50), 42(24), 83(11), 69(11), 68(8), 55(2), 52(0.9), 54(0.2), 67(0.2). The infrared spectrum (CCl$_4$ solution) showed major absorption maxima at 1695, 1620, 1435, 1370, 1340, 1250, 1080, 1000, 975, and 940 cm$^{-1}$ in the 2000–600 cm$^{-1}$ region.

B. Synthesis of Salts of APR

To APR (111 mg) in water (100 ml) was added hydrochloric acid (36.5 mg in 100 ml of water). The water was removed using a rotary evaporator to yield the hydrochloride salt of APR (greater than 95% pure) in greater than 95% yield.

EXAMPLE II

A. Odor Threshold Determination

Synthetic APR, prepared as described in Example IA, was subjected to organoleptic evaluation using a trained panel of 16 judges. Odor threshold determinations were carried out as described by Guadagni and Buttery, *Journal of Food Science*, Volume 43, pp 1346–1347 (1978). The odor threshold of APR in water solution was found to be 1 part in $10^{10}$ parts of water. The results of the odor threshold determinations are tabulated below:

| Concentration in parts per $10^9$ parts of water | % Correct Judgements | Total Number of Judgements |
| --- | --- | --- |
| 7 ppb | 100 | 16 |
| 3.5 | 94 | 16 |
| 0.9 | 94 | 16 |
| 0.35 | 95 | 19 |
| 0.18 | 86 | 52 |
| 0.09 | 75 | 81 |
| 0.045 | 65 | 113 |
| 0.023 | 53 | 94 |

B. Aroma Evaluation

A panel of 22 judges was asked to describe the aroma of a 0.05 ppm solution of APR in water. A similar test was carried with the cooked "scented" rice variety, Malagkit Sungsong (1982 crop from the Philippines). The panel's descriptions indicated that the odor of APR and the "scented" rice were very similar.

EXAMPLE III

Use of APR to Impart a "Scented" Rice Aroma

In an initial test, a panel of 22 judges was asked to evaluate the aroma of two varieties of rice, Calrose (a bland U.S. variety obtained from a local market in Berkeley, Calif. and the "scented" Malagkit Sungsong variety described in Example IIB. In this test 50 ml of one variety of cooked rice was placed in two flasks and one flask marked "Control." The other variety of rice (50 ml) was placed in a third identical flask. The three coded flasks were placed in the panel booth side by side and judges asked to match one of the two coded unknown samples with the "Control" sample. With 41 total judgements, the correct sample was matched 83% of the time indicating a significant deductable aroma difference between the two rice varieties.

In a second test, the two varieties of rice were compared as described above except that 25 ml of a 0.05 ppm water solution of synthetic APR (prepared as described in Example 1A) was added to each Calrose sample and 25 ml of odor-free water added to each Malagkit Sungsong sample. With 40 total judgements, the correct sample was matched only 62% of the time. This is only slightly greater than pure chance where the correct sample would be matched 50% of the time indicating that addition of APR to "bland" rice provides a rice having the aroma of the "scented" rice variety.

EXAMPLE IV

APR in Rice Varieties

The isolation, identification, and concentration of APR in ten rice varieties was determined as follows:

Steam Distillation Continuous Extraction of Rice

The rice (500 g, uncooked) was added to water (6 L) in a 12 L flask. A Likens-Nickerson steam distillation continuous extraction head was attached to the flask. Freshly distilled diethyl ether (125 ml) was used as the solvent in a 250 ml flask attached to the solvent arm of the head. The isolation was carried out at atmospheric pressure for 2 hours. The ether extract was dried over sodium sulfate and concentrated on a warm water bath, using low hold up distillation columns to 0.15 ml.

Isolation of Basic Fraction

The ether concentrate from above was dissolved in 50 ml of hexane. This solution was then extracted with 3N hydrochloric acid (3×25 ml). The combined acid extracts were washed with ether (1×50 ml). The washed acid extract was then neutralized with excess sodium bicarbonate under ether (100 ml) with ice bath cooling. The ether was separated and the aqueous layer extracted further (2×50 ml) with ether. The ether extracts were then combined, dried over sodium sulfate and concentrated to 0.01 ml.

Capillary Gas Chromatography Mass Spectrometry Analysis

This was carried out using a 150 m long by 0.64 mm i.d. Pyrex glass capillary column coated with Carbowax 20M. The effluent from the capillary column was introduced into the mass spectrometer (a modified Consolidated 21-620 cycloidal type) using a Llewellyn-Littlejohn type single stage silicone rubber membrane molecular separator. The GLC column was temperature programmed by holding at 50° C. for 30 minutes after injection and then increasing from 50° to 170° at 1° per minute and holding the temperature at the upper limit for 2 hours longer.

Concentration of APR in Rice Varieties

The concentration of APR present in the rice varieties studies was calculated from GLC peak areas. The concentrations found in the different rice is shown in the Table below. It can be seen that the Malagkit Sungsong has the highest concentration with 0.09 ppm and the Calrose the least amount with 0.006 ppm, a difference of a factor of 15. The higher values found for brown rices indicates that there may be some variation depending on the degree of milling.

| | 2-Acetyl-1-pyrroline Conc. ppm[a] | |
| --- | --- | --- |
| Variety | Milled Rice | Brown Rice |
| Malagkit Sungsong | 0.09 | 0.2 |
| IR841-76-1 | 0.07 | 0.2 |
| Khao Dawk Mali 105 | 0.07 | 0.2 |
| Milagrosa | 0.07 | |
| Basmati 370 | 0.06 | 0.17 |
| Seratus Malam | 0.06 | |
| Azucena | 0.04 | 0.16 |
| Hieri | 0.04 | 0.1 |

| Variety | 2-Acetyl-1-pyrroline Conc. ppm[a] | |
|---|---|---|
| | Milled Rice | Brown Rice |
| Texas Long Grain | <0.008 | |
| Calrose | <0.006 | |

[a] ppm = parts (weight) of compound per million ($10^6$) parts of rice (dry weight)

It is understood that the foregoing detailed description is given merely by way of illustration and that modifications and variations may be made therein without departing from the spirit and scope of the invention.

Having thus described our invention, we claim:

1. The compound 2-acetyl-1-pyrroline or salt thereof which is at least 95% pure.

2. A process for preparing a food composition which comprises adding to a food the substantially pure compound 2-acetyl-1-pyrroline or salt thereof in an amount sufficient to impart Basmati rice flavor to the composition.

3. The process of claim 2 wherein the amount of the compound sufficient to impart Basmati rice flavor is from about 0.001 to about 10 parts per million of the composition.

4. The process of claim 2 wherein the amount of the compound sufficient to impart Basmati rice flavor is from about 0.005 to about 0.5 parts per million of the composition.

5. The process of claim 2 wherein the compound is admixed with a carrier prior to the addition to the composition.

6. The process of claim 2 wherein the food is unscented rice.

7. The process of claim 2 wherein substantially pure 2-acetyl-1-pyrroline is synthetically prepared.

8. A flavoring composition comprising substantially pure 2-acetyl-1-pyrroline or salt thereof and a carrier.

* * * * *